United States Patent [19]

Hiraoka et al.

[11] Patent Number: 5,569,589
[45] Date of Patent: Oct. 29, 1996

[54] IMMUNOASSAY ELEMENT AND PROCESS AND IMMUNOASSAY

[75] Inventors: Toshikage Hiraoka, Asaka; Tetsuji Tanimoto, Tokyo; Yoshihiko Makino, Asaka; Tadashi Ninomiya, Tokyo; Naofumi Hora, Asaka; Yoshihiro Ashihara, Tokyo; Yukio Sudo; Toshihiro Mori, both of Asaka, all of Japan

[73] Assignees: Fuji Photo Film Co., Ltd., Kanagawa; Fujirebio Inc., Tokyo, both of Japan

[21] Appl. No.: 163,405

[22] Filed: Dec. 7, 1993

Related U.S. Application Data

[63] Continuation of Ser. No. 957,628, Oct. 6, 1992, abandoned, which is a continuation of Ser. No. 684,283, Apr. 12, 1991, abandoned.

[30] Foreign Application Priority Data

Apr. 13, 1990 [JP] Japan ........................... 2-96499

[51] Int. Cl.⁶ .................................................. G01N 33/53
[52] U.S. Cl. .................... 435/7.9; 435/7.91; 435/7.92; 435/14; 435/18; 435/22; 435/25; 435/28; 435/966; 435/969; 435/970; 436/518; 436/528; 436/529; 436/530; 436/531; 436/537; 436/807; 436/810; 422/56; 422/57
[58] Field of Search .................... 435/4, 7.1, 7.9, 435/7.91–7.92, 14, 18, 22, 25, 28, 805, 966, 969, 970; 436/518, 528, 529, 530, 531, 537, 807, 810; 422/56, 57

[56] References Cited

U.S. PATENT DOCUMENTS

| | | | |
|---|---|---|---|
| 4,089,747 | 5/1978 | Bruschi | 435/14 X |
| 4,144,306 | 3/1979 | Figueras | 435/14 X |
| 4,376,197 | 3/1983 | Wallenfels | 435/22 X |
| 4,544,631 | 10/1985 | Rauscher et al. | 435/14 |
| 4,782,018 | 11/1988 | Eikenberry et al. | 435/22 |
| 4,945,043 | 7/1990 | Gerber | 435/22 X |

FOREIGN PATENT DOCUMENTS

| | | | |
|---|---|---|---|
| 0104780 | 4/1984 | European Pat. Off. | 435/22 |
| 0347839 | 12/1989 | European Pat. Off. | 435/970 |
| 2377630 | 8/1978 | France | 422/56 |

OTHER PUBLICATIONS

Kaufman et al, Clinical Chemistry, vol. 26, No. 7, Jun. 1980, pp. 846–853.

N. Tietz, (ed.) Textbook of Clinical Chemistry (W B. Saunders Company 1986) pp. 729–734.

Primary Examiner—Carol A. Spiegel
Attorney, Agent, or Firm—McAulay Fisher Nissen Goldberg & Kiel, LLP

[57] ABSTRACT

An immunoassay element for quantitatively analyzing a ligand by determining the change in enzymatic activity caused by a reaction between the ligand, a linked product of the ligand and a high molecular weight compound and an enzyme-labelled antibody. The immunoassay element comprises a substrate layer containing a non-diffusible substrate which forms a diffusible material in the presence of the enzyme, and a reagent layer containing a fragmenting enzyme for further fragmenting the non-difussible material. Also provided is a process for quantitatively analyzing a ligand contained in a sample by the use of the immunoassay element.

21 Claims, 3 Drawing Sheets

IMMUNOASSAY ELEMENT AND PROCESS AND IMMUNOASSAY

This application is a continuation of application Ser. No. 07/957,628, filed Oct. 6, 1992, now abandoned, which, in turn, is a continuation of application Ser. No. 07/684,283, filed Apr. 12, 1991, now abandoned.

BACKGROUND OF THE INVENTION

1. Field of the Invention

The present invention relates to a dry immunoassay element in which a homogeneous enzyme immunoassay is utilized, and an immunoassay process in which the dry immunoassay element is used.

Analyses of the constituents originated from the living body or chemicals contained in the body fluids, such as blood and urine, are useful for diagnosing the condition of diseases or judging the developement of curing, and thus they occupy important parts in the field of clinical test. The so-called enzyme immunoassay has been known in the art as one of the methods for analyzing such a constituent (ligand) generally present in a small amount in the body fluids. The enzyme immunoassay may be classified into heterogeneous systems for which B/F (Bound/Free) separation must be effected, and homogeneous system for which B/F separation is not necessary. The reactions in the homogeneous system is based on the phenomenon that the enzymatic activity of the labelling enzyme is affected by some interference caused by binding of an antibody to the antigen (ligand), and the inhibition due to antigen-antibody binding is generally utilized. It is considered that the enzymatic activity is suppressed by a steric hindrance for binding the enzyme to the substrate or a change in three-dimensional structure of the enzyme, when the antibody which is generally a large molecule is bound to the antigen in the enzyme-labelled antigen. Meanwhile, in the routine clinical tests in which a number of test samples are to be handled, it is demanded that the individual samples should be analyzed rapidly by simple operations, more desirously by automated operation sequence.

2. Prior Art Statement

To comply with the demand, dry analysis elements have been proposed (see, for example, Unexamined Japanese Patent Publication Nos. 53888/1974 (corresponding to U.S. Pat. No. 3,992,158), 77356/1984 (corresponding to EP 0 097952A) and 102388/1984 and U.S. Pat. No. 4,459,358.)

A dry analysis element has been known, in which a homogeneous enzyme immunological reaction is utilized (see Unexamined Japanese Patent Publication No. 32136/1989 (corresponding to EP 0347839A)). This known dry analysis element comprises the following three ingredients in the same or other layers in a composite multi-layered structure:

(A) An antigen having a high molecular weight (a coupling product of a ligand or a derivative thereof with a high molecular weight compound; hereinafter referred to as "polymerized antigen");

(B) A water-insoluble high polymer substrate; and (C) A conjugate of an antibody against the ligand and an enzyme for the substrate.

The antigen supplied by spotting onto the analysis element binds to the antibody-enzyme conjugate through a competitive reaction with the reaction of the polymerized antigen. The complex of antigen-antibody-enzyme reacts with the water-insoluble high polymer substrate to form a soluble lower molecular weight product. On the other hand, the complex of polymerized antigen-antibody-enzyme formed by the binding with the polymerized antigen cannot exhibit the enzymatic activity to the high polymer substrate. Accordingly, as the quantity of the antigen in the sample is increased, the product produced by the enzymatic reaction increases. This product is allowed to diffuse into a detection layer where the quantity of the product is determined by measuring the optical density of an absorption resulted by the colored chemical group, to make it possible to analyze the antigen in the sample quantitatively.

However, in this known analysis element, since a high polymer substrate bound to a dye, such as dye-starch, is used and the dye bound to amylose which is the decomposition product formed by the action of amylase is determined, the high polymer substrate and the reaction product must be separated prior to the measurement or determination. It is, therefore, necessary to provide a light-shielding layer containing, for example, titanium dioxide fine particles between the reagent layer containing the unreacted substrate and the detection layer for receiving the reaction product. The analysis element having such a laminated structure is not preferred because it is necessary to take some time for the soluble reaction product formed in the reagent layer to be diffused into the detection layer, leading to the result that rapid quantitative determination, which is a major merit of the dry analysis element, cannot be carried out.

It is possible to improve the diffusibility of the reaction product by introducing a hydrophilic group, such as carboxyl or sulfo group, into the substrate to accelerate the diffusion of the reaction product. However, the site on which such a substituting group can be introduced is limited, and the introduction thereof might cause a demerit that the molecular extinction coefficient of the dye site governing the sensitivity of the analysis is lowered.

OBJECTS AND SUMMARY OF THE INVENTION

Accordingly, a first object of this invention is to provide an immunoassay element utilizing a homogeneous enzyme immunoassay for enabling a rapid analysis of an analyte at a high sensitivity by a simple operation.

A second object of this invention is to provide a process for quantitatively analyzing an analyte while using the aforementioned immunoassay element.

The first object of this invention is attained by the provision of an immunoassay element for quantitatively analyzing a ligand by determining the change in enzymatic activity caused by a reaction between said ligand, a linked product of said ligand with a high molecular weight compound and an enzyme-labelled antibody, said element comprising a substrate layer containing a non-diffusible substrate which forms a diffusible material in the presence of said enzyme, and a reagent layer containing a fragmenting enzyme for further fragmenting said diffusible material into a lower molecular weight product.

The linked product of the ligand and a high molecular weight compound (hereinafter referred to as "polymerized antigen") and the enzyme-labelled antibody may be contained in the substrate layer or a separate layer overlaid on the substrate layer.

The second object of this invention is attained by the provision of an immunoassay process for quantitatively analyzing an amount of a ligand in a sample by determining the change in linked activity caused by a reaction between said ligand, a coupling product of said ligand to a high molecular weight compound and an enzyme-labelled antibody, comprising the steps of:

(a) applying said sample into a substrate layer containing a non-diffusible substrate which forms a diffusible material in the presence of said enzyme;

(b) allowing to migrate said diffusible material formed in said substrate layer into a reagent layer containing a fragmenting enzyme for further decomposing to a lower molecular weihgt product; and (c) measuring the amount of said lower molecular weight product formed in said reagent layer.

The enzymatic activity of the enzyme of the enzyme-labelled antibody, which is bound to the polymerized antigen, to a non-diffusible substrate is hindered by the steric hindrance. On the contrary, the enzyme of the enzyme-labelled antibody, which is combined with the antigen contained in the sample (i.e. the ligand), keeps its original enzymatic activity to the non-diffusible substrate. As a result, the quantity of the diffusible material formed in the substrate layer is proportional to the quantity of the antigen contained in the sample. The diffusible material formed in the substrate layer migrates rapidly into the reagent layer, where it is further decomposed into a smaller molecular weight product. The lower molecular weight product may be detected in a detection layer. The unreacted non-diffusible substrate is held in the substrate layer.

DESCRIPTION OF PREFERRED EMBODIMENTS

Layer Construction of Immunoassay Element

Figure 1:
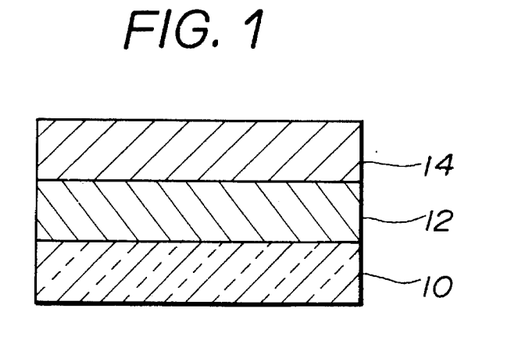
FIG. 1 is an illustration showing the principal structure of one embodiment of the immunoassay element according to this invention.

FIG. 1 shows an embodiment of the immunoassay element according to this invention.

Referring to FIG. 1, a transparent support is denoted by 10 on which laminated are reagent layer 12 and a substrate layer 14.

The substrate layer 14 is composed of a water-permeable material and contains a non-diffusible substrate for a labelling enzyme which forms a conjugate with the antibody. This substrate forms a diffusible material in the presence of an antigen-antibody-enzyme complex, which is produced in an amount propotional to the quantity of the ligand (antigen), i.e. the analyte to be determined quantitatively.

The reagent layer 12 is composed of a water-permeable material and contains a fragmenting enzyme. The fragmenting enzyme fragments the diffusible material, which is diffused or migrated from the substrate layer, into a lower molecular weight product. The substrate layer further contains a reagent composition for detecting the thus fragmented lower molecular weight product.

Analyte (Substance to be Analyzed)

The substance to be analyzed by the present invention (hereiafter referred simply as "analyte") is a ligand having an antigenic determinant and contained in the sample.

The analyte is not limited and many kinds of analyte may be analyzed by this invention, the typical examples include blood (whole blood, blood plasma, blood serum), lymph fluid and urine. It is preferred to preclude suspended particles, such as blood cells, when such particles are present. However, a sample may be directly spotted on the analysis element of this invention without precluding such suspended particles when the analysis element has a filter layer, according to a preferred embodiment of this invention.

Any ligands may be analyzed by the use of the analysis element of this invention, as far as each ligand acts as an antigen and an antibody therefor can be provided. Examples of such ligands include medicines such as digoxin, theophylline, phenobarbital, phenytoin, penicillin, amikacin, derivatives of these medicines (for example, complexes of medicines with living components, such as proteins), prostagladin and hormones such as testosterone, progesterone and thyroxine.

On the analysis element of this invention, competitive binding reactions between the ligand and the polymerized antigen to an enzyme-labelled antibody take places. Accordingly, it is preferable that the ligand has a relatively low molecular weight so as not to affect significant influence on the enzymatic activity. For instance, the analysis element of this invention exhibits its advantegeous merit when it is used for the analysis of a ligand having a molecular weight of less than about 20,000 daltons.

Polymerized Antigen

The polymerized antigen, i.e. the linked product of the ligand and a large molecule or high molecular weight compound, is bound to an antibody to suppress the activity of the enzyme which is conjugated with the antibody for labelling the latter.

It is preferable that the used high molecular weight compound is water-soluble and has a molecular weight of not less than 50,000 daltons. Examples of usable high molecular weight compound are proteins such as gelatine, hemocyanin and ferritin, and polyethylene glycol. It suffices that these compounds satisfy the aforementioned conditions when bound to the ligands, and those having relatively lower molecular weights, such as bovine serum albumin, can also be used by polymerizing them, for example, by auto-polymerization.

The method for linking the ligand to the high molecular weight compound may be selected in consideration of the functional groups of the both reactants. Utilizable functional groups include, for example, amino group, carboxyl group, hydroxyl group, thiol group, imidazole group and phenyl group. For example, amino groups may be linked to each other by a number of known methods, such as isocyanate method, glutaraldehyde method, difluorobenzene method and benzoquinone method. An amino groups may be linked to a carboxyl group by a method in which the carboxyl group is converted to succinylimide ester, or by other methods including the carbodiimide method, Woodward reagent method and the periodic acid oxidation method (Nakane method) in which the amino group is linked with a sugar chain. When a thiol group is utilized, one of the carboxyl groups is converted to succinylimide ester which is reacted with cysteine to introduce a thiol group and then both groups are linked to each other using a bifunctional linking reagent which reacts with the thiol group. The methods in which the phenyl group is utilized include the diazotization method and the alkylation method. The linking method is not limited to the aforementioned methods, and may be selected from the methods described in "Method in Immunology and Immunochemistry", vol. 1, (C. A. Williams, M. W. Chase, Academic Presss (1967)) or "KOSO MENEKI SOKUTEI-HO" (Enzyme Immunoassay), edited by Ishikawa, Kawai and Miyai, Igaku Shoin, 1978. The ligand may be linked to the high polymer compound at any desired ratio. After the completion of the linking reaction, the reaction product is refined by the gel filtration or the ion exchange chromatography, and may be dried by the lyophilizing process as desired.

The ligand per se may be polymerized to obtain a polymerized antigen. Polymerization of the ligand may be effected similar to the aforementioned linking methods. For example, the ligand may be polymerized by using a bifunctional cross-linking agent such as carbodiimide or glutaraldehyde.

In lieu of the ligand, the high molecular weight compound may be linked to a derivative of the ligand having immunological cross-reactivity to a corresponding antibody for the ligand. Meanwhile, the derivatives of the ligand include not only those which have analogous chemical structures but also those which exhibit analogous behaviors in their immunological reactivities. For instance, when an antibody against theophylline as the ligand cross-reacts immunologically with caffeine, derivatives of caffeine may also be used as materials for forming the polymerized antigen.

When the ligand or a derivative thereof has not a proper functional group to be linked to a high molecular weight compound, an amino group, a carboxyl group or a thiol group may be introduced into the ligand or the derivative thereof. Such a group may be introduced through a spacer to facilitate linking thereof to a high molecular weight compound. For example, when the ligand is theophylline, a carboxyl group may be introduced to obtain 8-propylcarboxyltheophylline which is linked to a high molecular weight compound.

Antibody

The antibody labelled with an enzyme is a specific antibody against the ligand which is an analyte. When a derivative of the ligand is used for forming the large molecule antigen, an antibody which reacts with the antigenic determinant common to the ligand and the derivative thereof. The antibody may be the one which can be obtained by ordinary process, a monoclonal antibody may be preferably used to improve the sensitivity. The antibody may be a fragment of F(ab')$_2$, Fab' or Fab.

Labelling Enzyme-Non-Diffusible Substrate-Fragmenting Enzyme

The enzyme bound to the antibody as the label decomposes the non-diffusible substrate formed of a high polymer to produce a diffusible product, which may be fragmented to a further lower molecular weight product by the action of the fragmenting enzyme.

The non-diffusible substrate is not dispersed into an aqueous sample liquid and neither dispersed nor migrated into the reagent layer by itself.

The fragmenting enzyme converts the diffusible product produced from the non-diffusible substrate by the action of the enzyme bound to the antibody as the label to form a lower molecular product which can be detected, the fragmenting enzyme being contained in the reagent layer of the analysis element of this invention.

A suitable combination may be selected so that an enzyme acts on the non-diffusible substrate to form a diffusible substance which is further decomposed by the fragmenting enzyme to produce a lower molecular weight product which is easily detected.

Labelling Enzyme

Examples of usable enzyme (labelling enzyme) include hydrolase which form diffusible oligomers from non-diffusible substrates composed of polymers, the specific example being glucosidase. Examples of glucosidase are α-amylase, β-amylase and dextranase. Other usable hydrolase are cellulase, collagenase, mannase, lipase and ribonuclease (RN).

The enzyme and the antibody may be conjugated similar to the linking between the high molecular weight compound and the antigen.

It is preferred that the enzyme is not affected by any hindering factor present in the sample, and that a competitive enzyme of same kind is not present in the sample. However, when an enzyme same as the labelling enzyme is present in the sample, the enzyme inhibitor may be used. Such an enzyme inhibitor may be the one which inhibits the enzyme in the sample at an extent which is larger than the extent for inhibiting the activity of the labelling enzyme. It is most preferable that the enzyme inhibitor inactivates entirely the enzyme in the sample and does not deactivate the labelling enzyme. However, in practical use, it suffices that the blank value is not raised at the determination step and the enzyme inhibitor may be inactivated to restore the activity of the enzyme in the sample after the completion of determination operation. It suffices that the enzyme inhibitor does not inhibit the enzyme in the enzyme-labelled antibody, and it can inhibit the activity of free enzyme. The enzyme inhibitor may be selected from known enzyme inhibitors so that the selected enzyme has the specific characteristics as aforementioned. Otherwise, an antibody against the enzyme which contained in a sample to cause a problem is prepared and used as an enzyme inhibitor.

Non-Diffusible Substrate

Examples of the substrate for said α-amylase, β-amylase or dextranase are carboxymethylated starch, starch, amylose or amylopectin.

When α-amylase is used as the enzyme for the enzyme-labelled antigen and glucoamylase or α-glucosidase (which will be described in detail hereinafter) is used as the fragmenting enzyme, a derivative of oligosaccharide prepared by modifying non-reduced terminal glucose residue with carboxymethyl group (disclosed in Unexamined Japanese Patent Publication No. 31699/1984 (corresponding to Chemical Abstracts, 101 (1984): 19761z) or an derivative of amylose (disclosed in Unexamined Japanese Patent Publication No. 39300/1984 (corresponding to EP 0104780A); Clinica Chemica Acta, 138, p21–29 (1984)) may be used. These modified substrates serve as the substrates for α-amylase, but do not serve as the substrates for glucoamylase or α-glucosidase.

Fragmenting Enzyme

The fragmenting enzyme may be an enzyme of the same kind as of the labelling enzyme. In such a case, it is preferred that the labelling enzyme is an endo-active enzyme which fragments the molecule intramolecularly to produce an oligomer, and that the fragmenting enzyme has an exo-activity to act the molecule at the terminal thereof to produce a monomer. For instance, when the non-diffusible substrate is a polymer (e.g. starch), a fragmenting enzyme for decomposing the diffusible oligomer (e.g. maltose) produced by the action of the labelling enzyme to a monomer (e.g. glucose) is used. Examples of the fragmenting enzyme include hydrolases for saccharides, specific examples being α-amylase, β-amylase, dextranase, glucoamylase and α-glucosidase.

When carboxymethyl cellulose is used as the non-diffusible substrate and cellulase is used as the labelling enzyme, Cl enzyme may be used as the fragmenting enzyme. Likewise, when the combination of galactane and galactanase is used, β-galactosidase may be used as the fragmenting enzyme; and when the combination of RNA and ribonuclease is used, exoribonuclease may be used as the fragmenting enzyme.

The combination of the labelling enzyme, the non-diffusible substrate and the fragmenting enzyme may be selected from the enzymes and substrates described in the known publications (for example, "Enzyme Handbook" (Bunji Maruo and Nobuo Tamiya, Asakura Shoten, 1982); and "Biochemical Handbook" (Nobumasa Imura et al., Maruzen, 1984).

The lower molecular weight product produced by fragmentation in the reagent layer by the action of the fragmenting enzyme may be optically detected by using a known detection reagent.

Any known methods may be employed for detecting the final glucose which is formed by the action of the aforementioned fragmenting enzyme, the examples being a method in which hydrogen peroxide formed by the oxidation of glucose in the presence of glucose oxidase is detected (e.g. the method wherein a Trinder reagent is used, as described in Ann. Clin. Biochem., 6, 24 (1964) and J. Clin. Pathol., 22, 246 (1969), the method wherein a Trinder reagent is used, as described in Unexamined Japanese Patent Publication No. 50991/1974 (corresponding to U.S. Pat. No. 3,886,045, U.S. Pat. No. 3,992,158) and Unexamined Japanese Patent Publication No. 164356/1980 (corresponding to U.S. Pat. No. 4,292,272), the method wherein a reagent containing a triaryl-substituted imidazole leuco dye is used, as described in Unexamined Japanese Patent Publication No. 26188/1978 (corresponding to U.S. Pat. No. 4,089,747) and Unexamined Japanese Patent Publication No. 45557/1983 (Chemical Abstracts, 99, (1983): 209284j), the method wherein a reagent containing an imidazole leuco dye substituted with a diarylmonoaralkyl, as described in Unexamined Japanese Patent Publication Nos. 193352/1984 (corresponding to EP 0122641A) and 224677/1985 (corresponding to U.S. Pat. No. 4,665,023)), a method wherein NADH produced in the presence of glucose dehydrogenase and NAD is detected, and a method wherein glucose-6-phosphate produced in the presence of hexokinase is detected. Amongst these detection methods, the most preferred is the method wherein glucose is oxidized in the presence of glucose oxidase to form hydrogen peroxide which is detected using peroxidase and a leuco dye because of its high detection sensitivity.

These detection reagents may be contained in the reagent layer together with the fragmenting enzyme, or may be contained in another layer disposed below the reagent layer (for example in a second reagent layer or a detection layer) to detect the produced lower molecular weight product. When a leuco dye is used, it is preferred that the dye is dispersed in the hydrophilic binder in the solution in a water-immiscible solvent in consideration of the stability of the formed dye.

Layer Structure of the Analysis Element

The dry immunoassay element of this invention may have a layer structure similar to those of various dry analysis elements. The element may be of a multi-layered construction including, in addition to the substrate layer and the reagent layer, a support, a spreading layer, a detection layer, a light-shielding layer, an adhesive layer, a water-absorbing layer, an undercoating layer and so on. Examples of such analysis elements are disclosed in the specifications of Unexamined Japanese Patent Publcication Nos. 53888/1974 (corresponding to U.S. Pat. No. 3,992,158), 40191/1976 (corresponding to U.S. Pat. No. 4,042,353) and 164356/1980 (corresponding to U.S. Pat. No. 4,292,272).

When a light-transmitting and water-impermeable support is used, the dry immunoassay element of this invention may practically be in the following construction. However, it is to be noted that the present invention is not limited to the following constructions.

(1) One having a reagent layer disposed on a support, and a substrate layer superposed on the reagent layer;

(2) One having the support, and a detection layer, a reagent layer and a substrate layer superposed in this order;

(3) One having the support, and a reagent layer, a light-shielding layer, and a substrate layer superposed in this order;

(4) One having the support, and a detection layer, a reagent layer, light-shielding layer and a substrate layer superposed in this order;

(5) One having the support, and a detection layer, a light-reflecting layer, a reagent layer and a substrate layer superposed in this order;

(6) One having the support, and a second reagent layer, a light-reflecting layer, a first reagent layer and a substrate layer superposed in this order; and (7) One having the support, and a detection layer, a second reagent layer, a light-reflecting layer, a first reagent layer and a substrate layer superposed in this order.

In the constructions set forth in (1) to (5), the reagent layer may be composed of plural layers. The reagent layer may be an immunological reaction layer which contains a component capable of taking part in a immunological reaction, as will be described hereinafter.

A water-absorbing layer may be disposed between the support and the reagent or detection layer. Filtering layers may be interposed between the adjacent layers. A spreading layer may be disposd on the substrate layer, or the substrate layer may be a spreading layer to act also as a spreading layer.

Substrate Layer

The substrate layer 14 is composed of a water-permeable layer and contains a non-diffusible substrate which is a substrate for the enzyme labelling the antibody.

In order to ensure water-permeability of the substrate layer, it is preferable that the substrate layer is composed of a porous medium or a layer composed of a hydrophilic polymer binder.

The porous layer may be fibrous or non-fibrous. As the fibrous material, filter paper, non-woven cloth, woven cloth (e.g. plain woven cloth), knitted cloth (e.g. tricot knitted cloth) or filter paper made of glass fibers may be used. Examples of the non-fibrous material include a membrane filter composed of cellulose acetate described in Unexamined Japanese Patent Publication No. 53888/1974 (corresponding to U.S. Pat. No. 3,992,158), and a particulate structure layer containing interconnected spaces and composed of inorganic or organic fine particles as disclosed in Unexamined Japanese Patent Publication Nos. 90859/1980 (corresponding to U.S. Pat. No. 4,258,001) and 70163/1983 (correponding to U.S. Pat. No. 4,486,537). A laminated structure made of partially bonded multiple porous layers may also be preferably used, examples of such structure being disclosed in Unexamined Japanese Patent Publication Nos. 4549/1986 (corresponding to EP 0166365A), 116258/1987 (Chemical Abstracts, 108, (1988): 3041y), 138756/1987 (EP 0226465A), 138757/1987 (EP 0226465A) and 138758/1987 (EP 0226465A).

The porous layer may be a spreading layer having a so-called metering function to spread a liquid over an area substantially in proportion to the volume of the fed liquid. Preferable materials for the spreading layer are woven and knitted fabrics. The woven fabrics or like may be subjected to the glow discharge treatment as described in Unexamined Japanese Patent publication No. 66359/1982 (corresponding to GB 2,087,974A and U.S. Pat. No. 4,783,315). In order to adjust the area or rate for spreading, the spreading layer may contain a hydrophilic polymer or a surfactant as described in Unexamined Japanese Patent publication Nos. 222770/1985 (corresponding to EP 0162301A), 219397/1988 (corresponding to DE 37 17 913A), 112999/1988 (corresponding to DE 37 17 913A), and 182652/1987 (corresponding to DE 37 17 913A).

It is a convenient method wherein the substrate is impregnated into or coated on a porous membrane made of, for example, paper, cloth or a high polymer and then the composite is applied on another water-permeable layer, for example, a reagent layer disposed on the support by a method as described in Unexamined Japanese Patent publication No. 164356/1980 (corresponding to U.S. Pat. No. 4,292,272). A further method comprises the steps of bonding a porous layer on another water-permeable layer (for example a reagent layer) by a method as described above, and coating a composition containing the substrate on the porous layer. Any known methods may be employed for the impregnation or coating on the porous layer. Coating may be effected by selecting a suitable method, for example, dip coating, doctor coating, hopper coating and curtain coating.

Although the thickness of the substrate layer made by any of the aforementioned methods is not limited, proper thickness ranges within 1 µm to 50 µm, preferably from 2 µm to 30 µm, when the layer is provided as a coating layer. When it is provided by another method, for example by piling of a laminate, the thickness thereof may be varied within a wide range of from several tens µm to several hundreds µm.

When the substrate layer is constituted of a water-permeable layer composed of a hydrophilic polymer binder, the specific examples of usable hydrophilic polymers being gelatin and derivatives thereof (such as phthalated gelatin), derivatives of cellulose (such as hydroxyethyl cellulose), agarose, sodium alginate, acrylamide copolymers, methacrylamide copolymers, copolymers of acryl amides or methacrylamides with various vinyl monomers, polyhydroxyethyl methacrylate, polyvinyl alcohol, polyvinyl pyrrolidone, sodium polyacrylate, and copolymers of acrylic acid with various vinyl monomers.

The substratre layer composed of a hydrophilic polymer binder may be provided by coating an aqueous solution or dispersion of the substrate, an additional other reagent composition and a hydrophilic polymer binder on another layer, such as a support or a detection layer, and then drying the coated solution or dispersion, as disclosed in the specifications of Japanese Patent Publication No. 21677/1988 (corresponding to U.S. Pat. No. 3,992,158), Unexamined Japanese Patent publication Nos. 164356/1980 (corresponding to U.S. Pat. No. 4,292,272), 101398/1979 (corresponding to U.S. Pat. No. 4,132,528), and 292063/1986 (Chemical Abstracts, 106, 210567y). The thickness of the dried substrate layer containing a hydrophilic polymer as the binder ranges from about 2 µm to about 50 µm, preferably from about 4 µm to about 30 µm, and the coverage thereof ranges from about 2 g/m$^2$ to about 50 g/m$^2$, preferably from about 4 g/m$^2$ to about 30 g/m$^2$.

With the aim to improving the characteristics, such as coatability, diffusibility of the diffusible material, reactivity and storage stability, the substrate layer may be added with, in addition to the non-diffusible substrate, various organic or inorganic additives, the examples being activators for enzyme, coenzymes, surfactants, pH buffer reagents, fine particles, antioxidants, etc. As the examples of buffer system which may be contained in the substrate layer, it may be mentioned to pH buffer reagents as described in "KAGAKU BINRAN, KISOHEN" (edited by Japanese Chemical Society, MARUZEN, Tokyo, 1966), pp1312–1320; R. M. C. Dawson et al., "Data for Biological Research", 2nd Edition (Oxford at the Clarendon Press, 1969), pp476–508; "Biochemistry", 5, pp467–477 (1966); and "Analytical Biochemistry", 104, pp300–310 (1980). Specific examples of usable buffers are buffer reagents containing tris(hydroxymethyl)aminomethane (Tris), buffer reagents containing phosphates, buffer solutions containing borates, buffer reagents containing citric acid or citrates, buffer reagents containing glycine, buffer solutions containing Bicine, and buffer reagents containing HEPES.

Reagent Layer

The reagent layer 12 contains a fragmenting enzyme and may contain a detection reagent composition for detecting the lower molecular weight product formed by the action of the fragmenting enzyme as desired.

The reagent layer is composed of a water-permeable layer which is preferably a continuous layer made of a hydrophilic polymer binder, similar to the water-permeable layers as described in the description of the substrate layer. The used hydrophilic polymer binder may be determined in consideration of the diffusible product formed in the substrate layer and the coloring reagent contained in the reagent layer.

Support

The support 10 may be light-nontransmitting (opaque), light-semi-transmitting (translucent) or light-transmitting (transparent), and it is generally preferable that the support is light-trasmitting and water-impermeable.

Preferable materials for the light-transmitting and water-impermeable support are polyethylene terephthalate and polystyrene. In general, an undercoating is provided or the support is subjected to hydrophilization treatment in order that the hydrophilic layer adheres firmly.

Immunological Reaction Layer

The substrate layer 14 shown in FIG. 1 may contain a polymerized antigen and enzyme-labelled antibody, in addition to the non-diffusible substrate, to form an immunological reaction layer in which an immunological reaction takes place. With such a construction, a homogeneous enzyme immunological reaction takes place in the element only by spotting a sample on the element.

Otherwise, any one of the polymerized antigen or the enzyme-labelled antibody is contained in the substrate layer, and the other is contained in a water-permeable layer laminated on the substrate layer.

Alternatively, the polymerized antigen and the enzyme-labelled antibody may be contained separately in plural separate layers.

Figure 2:
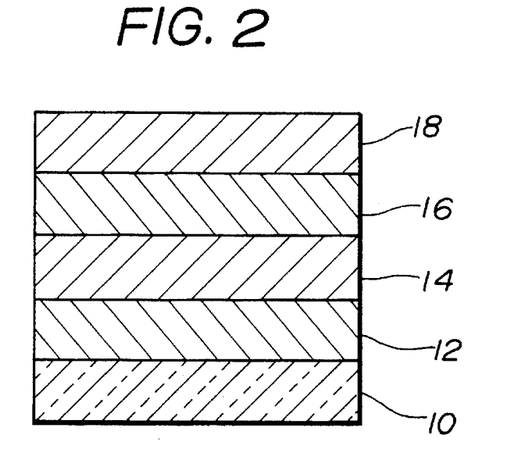
FIG. 2 is an illustration showing another embodiment of the immunoassay element according to this invention.

For example, as shown in FIG. 2, a water-permeable layer 16 containing the enzyme-labelled antibody may be disposed on the substrate layer 14, and another water-permeable layer 18 containing the polymerized antigen may be laminated on the layer 16 to form the immunoassay element of the invention. In this case, the ligand (antigen) in the sample diffuses and migrates into the layer 16 together with the polymerized antigen contained in the layer 18. In the layer 16, the ligand and the polymerized antigen bind respectively with the antibody of the enzyme-labelled antibody, and then migrate into the substrate layer.

Alternatively, a polymerized antigen and an enzyme-labelled antibody may be contained in a separate layer in the substantially dry state or in the substantial absence of water.

Figure 3:
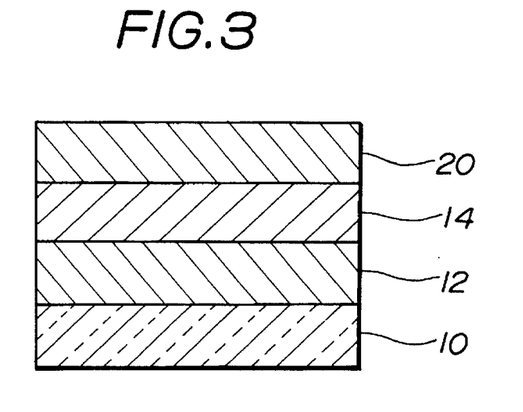
FIG. 3 is an illustration showing a further embodiment of the immunoassay element according to this invention.

In detail, as shown in FIG. 3, the analysis element of the invention may comprise a water-permeable layer 20 superposed on the substrate layer 14, the water-permeable layer 20 containing a polymerized antigen and an enzyme-labelled antibody in the substantially dry state or in the substantial absence of water. In such an embodiment, when a sample containing an analyte in an aqueous medium is spotted on the layer 20, the ligand (antigen) in the sample and the polymerized antigen form complexes with the enzyme-labelled antigen, and the formed complexes migrate into the substrate layer 14. In order to contain a large molecule antigen and an enzyme-labelled antigen together in a separate layer in the substantially dry state or in the substantial absence of water, either one or both of the polymerized antigen and the enzyme-labelled antibody may be dissolved or dispersed in a non-aqueous medium, such as an alcohol (e.g. ethanol) and then the solution or dispersion is impregnated in the water-permeable layer.

Process for Preparing the Immunoassay Element

The dry immunoassay element of the invention may be prepared by any of the known processes described in the specifications of aforequoted prior patents.

The analysis element of the invention may be cut into a square piece having sides each ranging from about 15 mm to about 30 mm or a disk having a substantially equal area, and it is preferred, in view of the preparation, packaging, shipping, storage and measuring operations, that it is contained in a slide frame disclosed, for example, in Japanese Patent Publication No. 28331/1982 (corresponding to U.S. Pat. No. 4,169,751), Unexamined Japanese Utility Model Publication No. 142454/1981 (corresponding to U.S. Pat. No. 4,387,990), Unexamined Japanese Patent publication No. 63452/1982, Unexamined Japanese Utility Model Publication No. 32350/1983 and Unexamined Japanese Patent Publication No. 501144/1983 (corresponding to International Publication WO 83/00391) to be used as a slide for chemical analysis. For the convenience of some uses, it may be formed in a tape shape which is contained in a cassette or magazine, or a small piece thereof may be applied on or contained in a card having an opening.

Analyzing Method Using the Immunoassay Element

The analysis element of the invention may be used for the quantitative analysis of an analyte ligand in an sample liquid by using it through the operations described in the specification of the aforequoted prior patents.

For example, about 5 µl to about 30 µl, preferably 8 µl to 15 µl, of an aqueous sample liquid, such as serum, plasma or urine, is spotted or otherwise fed on the substrate layer 14. The analysis element spotted with the sample liquid is then incubated at a constant temperature of from about 20° C. to about 45° C., preferably at a constant temperature of from about 30° C. to about 40° C., for 1 to 10 minutes. The reflected light of the color or the change in color in the element may be measured from the light-transmitting support side, and the quantity of the ligand contained in the sample can be determined using a preliminarily drawn calibration curve based on the principle of colorimetry. The volume of the spotted liquid sample and the time and temperature for incubation are maintained constant to improve the accuracy in quantitative analysis.

The measuring operation may be carried out while using the chemical analysis apparatus described in Unexamined Japanese Patent Publication Nos. 125543/1985, 220862/1985, 294367/1986 and 161867/1983 (the last-mentioned Publication corresponding to U.S. Pat. No. 4,424,191) to realize a quantitative analysis at a high accuracy by extremely easy operations.

Meantime, a semi-quantitative analysis may be conducted by judging the degree of coloring by naked eye if such visual judgment is adequate for the object or required accuracy.

When the anaysis element does not contain the polymerized antigen and the enzyme-labelled antibody, the aqueous sample liquid is mixed with a solution containing the polymerized antigen and the enzyme-labelled antibody to complete the binding reaction, and then spotted on the substrate layer.

SYNTHESIS EXAMPLE (1) Synthesis of Enzyme-Labelled Antibody (1-A) Preparation of CHM Amylase 5 mg of *Bacillus subtilis* amylase was dissolved in 1 ml of a 0.1M glycerophosphate (pH 6.3), and 100 µl of a 2 mg/ml solution of [4-(maleimidomethyl)cyclohexane-1-carboxylic acid] succinimide ester (CHMS) in DMF was added thereto to react at room temperature for an hour. The reaction mixture was applied to a SEPHADEX G-25 (produced by Pharmacia Co.) column through which flown was a 0.1M glycerophosphate (pH 6.3) to take the passing fraction to obtain 4-(maleimidomethyl)cyclohexane-1-carboxyamido amylase (CHM amylase).

(1-B) Preparation of Anti-Theophylline Mouse IgG-Fab'

300 μg of papain was added to 10 mg of anti-theophylline mouse IgG (in 2 ml of 0.1M acetate buffer (pH 5.5)), and stirred at 37° C. for 18 hours. A 0.1N NaOH solution was added to the reaction liquid to adjust the pH value thereof to pH 6.0, and then put into a AcA-44 produced by Rhone Poulenc SA gel column preliminarily equilibrated with a 0.1M phosphate buffer (pH 6.3) containing 1 mM EDTA, followed by elution with the aforementioned phosphate buffer solution. The peak portion of the eluate having molecular weights of approximetely 100,000 was collected and concentrated to 1 ml to obtain the objective anti-theophylline mouse IgGF (ab')$_2$.

(1-C) Preparation of Bound of α-Amylase-Anti-Theophylline Mouse IgG-Fab'

100 μl of a 10 mg/ml aqueous solution of 2-mercaptoethylamine HCl salt was added to 1 ml of a 0.1M phosphate buffer (containing 1 mM EDTA, pH 6.0) containing 6 mg of the anti-theophylline mouse IgG-F(ab')$_2$ prepared in the step (1-B), and stirred at 37° C. for 90 minutes. The reaction Mixture was subjected to gel filtration by a SEPHADEX G-25 produced by Pharmacia Co.) column which was preliminarily equilibrated with a 0.1M phosphate buffer (pH 6.3) to remove unreacted 2-mercaptoethylamine to obtain HS-Fab'. 2 mg of the CHM α-amylase prepared by the step (1-A) was added to HS-Fab' to react at 37° C. for 90 minutes. The reaction mixture is then subjected to gel filtration using the AcA-34 (produced by Rhone Poulenc SA) column equilibrated with a 0.1M phosphate buffered 5 mM calcium chloride solution (pH 7.0) to collect a fraction having molecular weights of not less than 200,000, and the fraction was concentrated to obtain the objective conjugate of α-amylase and anti-theophylline mouse IgG-Fab'.

(2) Synthesis of Polymerized Antigen (Equine Ferritin-Theophylline Conjugate)

5 mg of 8-propylcarboxytheophylline was dissolved in 1 ml of dimethylformamide (DMF), and 3 mg of N-hydroxysuccinimide and 5 mg of water-soluble carbodiimide was added thereto, followed by stirring at room temperature for 2 hours, to prepare activated theophylline. 10 mg of equine ferritin was dissolved in 1 ml of a 0.1M aqueous solution of sodium hydrogencarbonate and added with 500 μl of the aforementioned activated theophylline solution. After allowing to stand at room temperature for an hour, the mixed solution was flown through a Sephadex-G-25 (produced by Pharmacia Co.) column which was preliminarily equilibrated with a phosphate bufferd saline (PBS, pH 7.0) to remove unreacted substances, whereby 9 mg of the objective polymerized antigen (equine ferritin-theophylline conjugate) was obtained.

(3) Synthesis of Polymerized Antigen (Theophylline Bovine Serum Albumin Conjugate)

5 mg of 8-propylcarboxytheophylline was dissolved in 1 ml of DMF, and added with 3 mg of N-hydroxysuccinimide and 5 mg of water-soluble carbodiimide, followed by stirring at room temperature for 2 hours, to obtain activated theophylline. 10 mg of bovine serum albumin (BSA) was dissolved in 1 ml of a 0.1M aqueous solution of sodium hydrogencarbonate and added with 500 μl of the aforementioned activated theophylline solution. The mixed solution was allowed to stand at room temperature for an hour, and then unreacted substances were removed through a SEPHADEX G-25 (produced by Pharmacia Co.) column preliminarily equilibrated with PBS to obtain 9 mg of the objective large molecule antigen (theophylline-BSA conjugate)

EXAMPLE 1

On a colorless and transparent polyethylene terephthalate (PET) sheet (support) coated with a gelatin undercoating and having a thickness of 180 μm, coated was a reagent solution containing a cross-linking reagent, followed by drying, to form a reagent layer so that respective components had the covergages as set forth below.

| | |
|---|---|
| Alkaline-treated Gelatin | 14.5 g/m$^2$ |
| Nonylphenoxypolyethoxyethanol (Containing 9 to 10 (average) of Oxyethylene Units) | 0.2 g/m$^2$ |
| Glucose oxidase | 5,000 U/m$^2$ |
| Peroxidase | 15,000 U/m$^2$ |
| Glucoamylase | 5,000 U/m$^2$ |
| 2-(4-hydroxy-3,5-dimethoxyphenyl)-4-[4-(dimethylamino)phenyl]-5-phenytyl-imidazole (Leuco Dye) Acetate | 0.38 g/m$^2$ |
| Bis[(vinylsulfonylmethylcarbonyl)amino]-methane | 0.1 g/m$^2$ |

An adhesive layer was coated on the reagent layer to have the following coverage, and then dried.

| | |
|---|---|
| Alkaline-treated Gelatin | 14.5 g/m$^2$ |
| Bis[(vinylsulfonylmethylcarbonyl)amino]-methane | 0.1 g/m$^2$ |

Then, an aqueous solution containing the following reagent was coated over the surface of the adhesive layer to have the following coverges to swell the gelatin layer on which laminated, by pressing uniformly with a light pressure, a tricot knitted cloth made by knitting PET spun yarn of 36 gage corresponding to 50 deniers and having a thickness of about 250 μm to form a porous spreading layer.

| | |
|---|---|
| Nonylphenoxypolyethoxyethanol (Containing 9 to 10 (average) of Oxyethylene Units) | 0.15 g/m$^2$ |
| Bis[(vinylsulfonylmethylcarbonyl)amino]-methane | 0.4 g/m$^2$ |

Thereafter, a subsrate layer was formed by coating a substrate, followed by drying, to have the following coverages, whereby a multi-layered analysis element for the quantitative analysis of theophylline was prepared.

| | |
|---|---|
| Carboxymethyl Starch | 4 g/m$^2$ |
| Nonylphenoxypolyethoxyethanol (Containing 9 to 10 (average) of Oxyethylene Units) | 0.2 g/m$^2$ |

The thus prepared element was cut into tips each having 1.5 cm square, and each tip was contained in a slide frame described in Unexamined Japanese Patent Publication No. 63452/1982 to prepare a multi-layered dry slide A for the analysis of theophylline.

Figure 4:
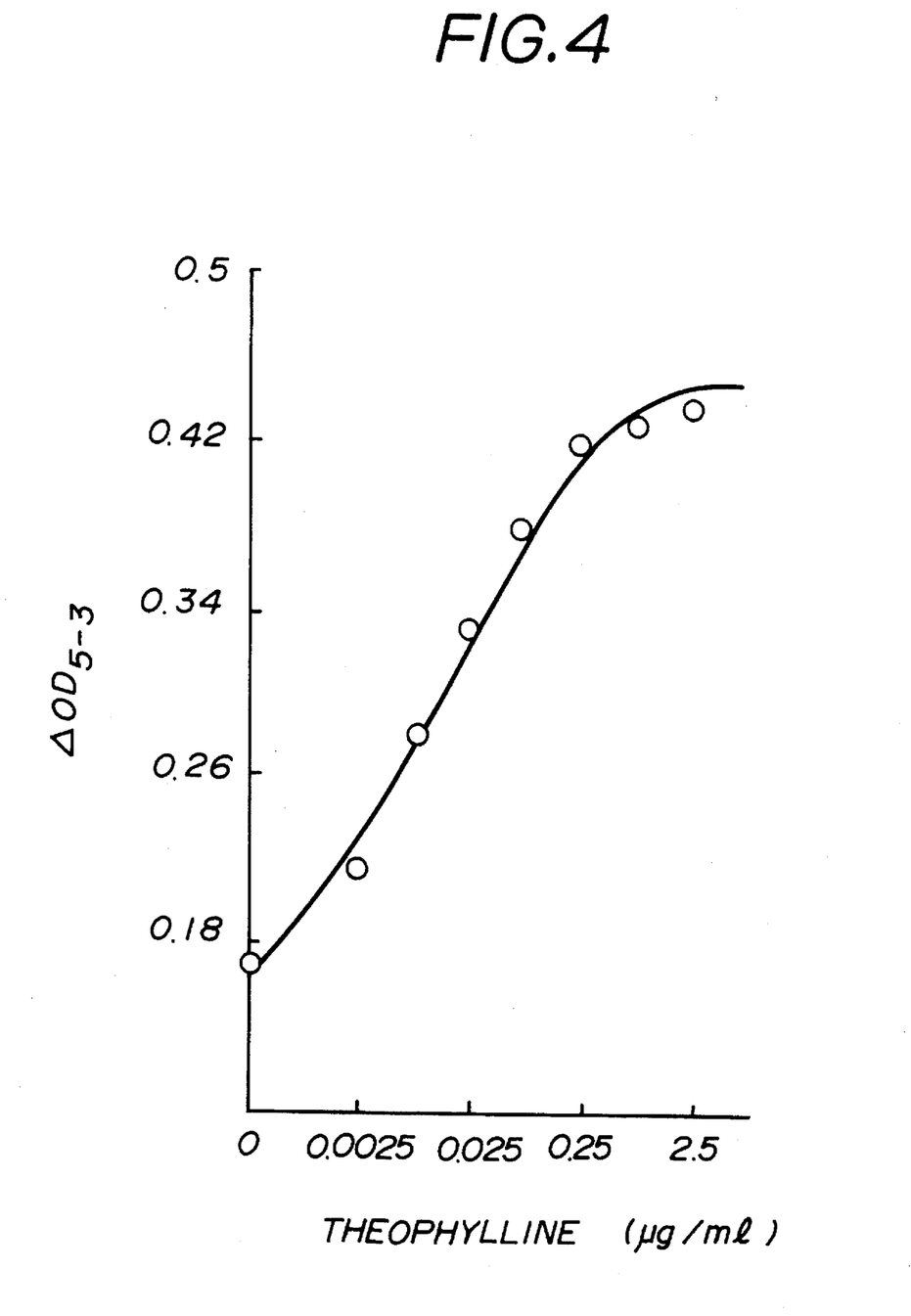
FIG. 4 is a graphic representation showing the calibration curve when the immunoassay element of Example 1 is used.

Test for Appraisal of the Properties 0.1 mg/ml for each of the amylase-anti-theophylline IgG conjugate prepared by the Synthesis Example (1) and the theophylline-equine ferritin conjugate prepared by synthesis Example (2) was added to a 50 mM glycerophosphate buffer (pH 7) containing a predetermined quantity of theophylline, and incubated at 37° C. for 20 minutes. 10 μl of each solution was spotted on the aforementioned slide A. The slide A was maintained at 37° C., and the optical density of the reflected light having a wavelength of 650 nm was measured from the support side. The difference in optical density ($\Delta OD_{5-3}$) of the reflected lights measured respectively after the lapse of 3 minutes and 5 minutes is shown in FIG. 4.

EXAMPLE 2

Similar to Example 1, a multi-layered analysis element having a tricot knitted cloth layer was prepared. On the tricot knitted cloth layer, which served both as a substrate layer and a spreading layer, coated was a solution of the amylase-anti-theophylline IgG conjugate (Synthesis Example (1)) in ethanol to have a coverage of 3 mg/m², followed by drying, to prepare a multi-layered immunoassay slide B for the analysis of theophylline.

Test for Appraisal of the Properties

Figure 5:
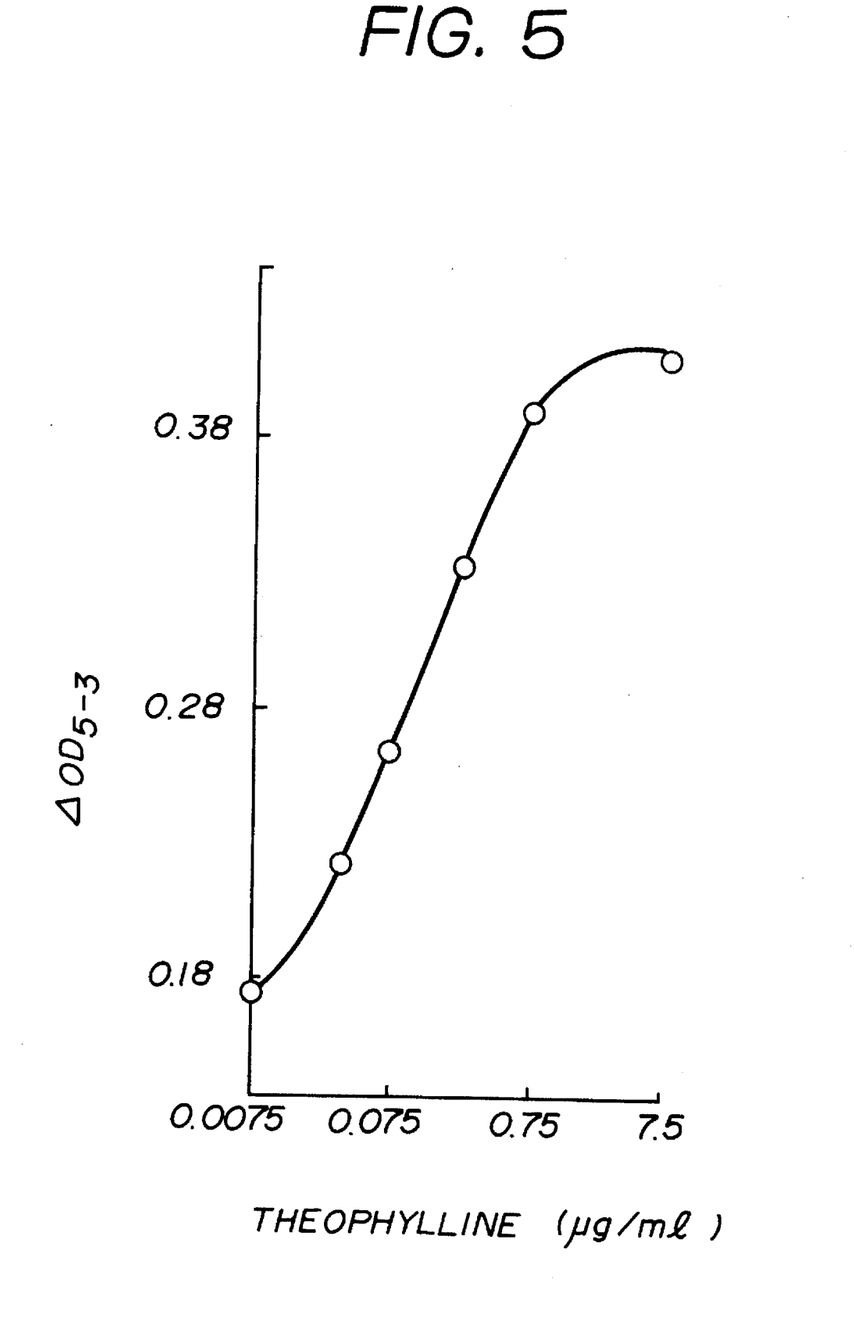
FIG. 5 is a graphic representation showing the calibration curve when the immunoassay element of Example 2 is used.

10 μl of a 50 mM glycerophosphate buffer solution (pH 7) containing the theophylline-BSA bound (0.1 mg/ml) prepared by Synthesis Example (3) and also containing a known quantity of theophylline was spotted on the slide B. The slide B was maintained at 37° C., and the optical density of the relfected light having a wavelength of 650 nm was measured from the PET support side. FIG. 5 shows the difference in optical density ($\Delta OD_{5-3}$) between the optical density of the reflected light measured after the lapse of 3 minutes from spotting and the optical density of the reflected light measured after the lapse of 5 minutes from spotting. It should be appreciated from the calibration curve shown in FIG. 5 that the dry immunoassay element for the analysis of theophylline, prepared in accordance with the present invention, can be used for quntitative analysis of theophylline to give accurate result.

EXAMPLE 3

Similar to Example 1, a multi-layered analysis element having a tricot knitted cloth layer was prepared. On the tricot knitted cloth layer, which served both as a substrate layer and a spreading layer, coated were 3 mg/m² of the theophylline-BSA conjugate (Synthesis Example (3)) by impregnating an aqueous solution of the theophylline-BSA conjugate and 3 mg/m² of the amylase-anti-theophylline IgG conjugate (synthesis Example (1)) by impregnating an ethanol solution of the amylase-anti-theophylline IgG conjugate, followed by drying, to prepare a multi-layered immunoassay slide C for the analysis of theophylline.

10 μl of a 50 mM glycerophosphate buffer solution (pH 7) containing a known quantity of theophylline was spotted on the slide C. The slide C was maintained at 37° C., and the optical density of the relfected light having a wavelength of 650 nm was measured from the support side. A calibration curve was drawn by calculating the difference in optical density ($\Delta OD_{5-3}$) between the optical density of the reflected light measured after the lapse of 3 minutes from spotting and the optical density of the reflected light measured after the lapse of 5 minutes from spotting. It was found that theophylline could be quantitatively analyzed at high accuracy similar to Example 2.

What is claimed is:

1. An immunoassay element for quantitatively analyzing a ligand by determining a change in enzymatic activity of a labelling enzyme caused by a competitive reaction between 1. the ligand and 2. a linked product comprising
      (i) the ligand or a derivative thereof having a common antigenic determinant with the ligand and
      (ii) a high molecular weight compound having a molecular weight of not less than 50,000 daltons for specific binding to 3. an enzyme labelled antibody which can react and bind specifically with the ligand and the linked product, wherein the high molecular weight compound sterically hinders enzymatic activity in specific binding complexes comprising the enzyme labelled antibody and the linked product;

said element comprising:
      (a) a substrate layer comprising a non-diffusible substrate composed of a polymer which is capable of being digested by the labelling enzyme into a diffusible oligomer, which is capable of migrating out of the substrate layer; and
      (b) a reagent layer comprising a fragmenting enzyme for further fragmenting the diffusible oligomer into a detectable monomer, the reagent layer also comprising a reagent composition which react with the detectable monomer to form a dye having an absorption peak in the visible wavelength range;

wherein the labelling enzyme is an endo-active hydrolase to digest the polymer into the diffusible oligomer and the fragmenting enzyme is an exo-active hydrolase which is capable of digesting the diffusible oligomer into detectable monomer.

2. The immunoassay element according to claim 1 wherein the enzyme-labelled antibody is contained in the substrate layer or a layer superposed on the substrate layer.

3. The immunoassay element according to claim 1 wherein the linked product is contained in said substrate layer or a layer superposed on the substrate layer.

4. The immunoassay element according to claim 1 wherein the enzyme-labelled antibody and the linked product are contained in the substrate layer.

5. The immunoassay element according to claim 1 wherein the labelling enzyme is an endo-active glucosidase and the fragmenting enzyme is an exo-active glucosidase.

6. The immunoassay element according to claim 5 wherein the non-diffusible substrate is a polysaccharide which is a polymer of glucose units;

wherein the labelling enzyme is an endo-active glucosidase being capable of digesting the polysaccharide to produce an oligomer of the glucose units;

wherein the fragmenting enzyme is an exo-active glucosidase being capable of digesting the oligomer to produce a monomer of the glucose; and wherein the detectable monomer is glucose monomer.

7. The immunoassay element according to claim 1 wherein the reagent composition reacts with the detectable monomer to form a peroxide.

8. The immunoassay element according to claim 7 wherein the reagent composition contains a leuco dye which colors upon oxidation.

9. The immunoassay element according to claim 8 wherein the reagent layer contains a hydrophilic binder, and wherein the reagent composition contains a dispersion of a solution of leuco dye in a water-insoluble solvent in the hydrophilic binder.

10. The immunoassay element according to claim 9 wherein the reagent composition contains a glucose oxidase, a peroxidase and a leuco dye.

11. The immunoassay element according to claim 1, wherein said substrate layer is composed of fibrous material and said reagent layer is composed of hydrophilic polymer binder.

12. The immunoassay element according to claim 11 wherein said fibrous material is selected from the group consisting of a woven cloth and a knitted cloth.

13. An immunoassay process for quantitatively analyzing an amount of a ligand in a sample by determining a change in enzymatic activity of a labelling enzyme comprising contacting the sample with the immunoassay element of claim 1 which element comprises the linked product and the enzyme labelled antibody whereby a competitive reaction occurs to produce a detectable monomer, and measuring the amount of detectable monomer product.

14. The immunoassay process according to claim 13, wherein said substrate layer is composed of fibrous material and said reagent layer is composed of a hydrophilic polymer binder.

15. The immunoassay process according to claim 14, wherein said fibrous material is selected from the group consisting of a woven cloth and a knitted cloth.

16. An immunoassay element for quantitatively analyzing a ligand by determining a change in enzymatic activity of a labelling enzyme caused by a competitive reaction between
  1. the ligand and
  2. a linked product comprising
     (i) the ligand or a derivative thereof having a common antigenic determinant with the ligand and
     (ii) a high molecular weight compound having a molecular weight of not less than 50,000 daltons for specific binding to
  3. an enzyme labelled antibody which can react and bind specifically with the ligand and the linked product, wherein the high molecular weight compound sterically hinders enzymatic activity in specific binding complexes comprising the enzyme labelled antibody and the linked product;
said element comprising:

(a) a substrate layer comprising a non-diffusible substrate composed of a polymer which is capable of being digested by the labelling enzyme into a diffusible oligomer, which is capable of migrating out of the substrate layer; and
  (b) a reagent layer comprising a fragmenting enzyme for further fragmenting the diffusible oligomer into a detectable monomer; and
  (c) a water-permeable layer which contains a reagent composition which reacts with the detectable monomer to form a dye having an absorption peak in the visible wavelength range;

wherein the labelling enzyme is an endo-active hydrolase to digest the polymer into the diffusible oligomer and the fragmenting enzyme is an exo-active hydrolase which is capable of digesting the diffusible oligomer into the detectable monomer.

17. The immunoassay element according to claim 16 wherein the reagent composition reacts with the detectable monomer to form a peroxide.

18. The immunoassay element according to claim 17 wherein the reagent composition contains a leuco dye which colors upon oxidation.

19. The immunoassay element according to claim 18 wherein the reagent layer contains a hydrophilic binder, and wherein the reagent composition contains a dispersion of a solution of leuco dye in a water-insoluble solvent in the hydrophilic binder.

20. The immunoassay element according to claim 16, wherein said substrate layer is composed of fibrous material and said reagent layer is composed of a hydrophilic polymer binder.

21. The immunoassay element according to claim 20, wherein said fibrous material is any of a woven cloth and a knitted cloth.

* * * * *